(12) United States Patent
Eini et al.

(10) Patent No.: US 9,168,224 B2
(45) Date of Patent: Oct. 27, 2015

(54) PIMECROLIMUS FOAM COMPOSITION CONTAINING HEXYLENE GLYCOL, OPTIONALLY OLEYL ALCOHOL, DIMETHYLISOSORBIDE AND/OR MEDIUM CHAIN TRIGLYCERIDES

(75) Inventors: Meir Eini, Ness Ziona (IL); Doron Friedman, Karmei Yosef (IL); Stefan Hirsch, Lörrach (DE); Sabine Meyenburg, Inzlingen (DE); Nabila Sekkat, Basel (MA); Dov Tamarkin, Maccabim (IL)

(73) Assignee: Meda Pharma SARL, Luxembourg (LU)

( * ) Notice: Subject to any disclaimer, the term of this patent is extended or adjusted under 35 U.S.C. 154(b) by 2044 days.

(21) Appl. No.: 11/547,226

(22) PCT Filed: Apr. 7, 2005

(86) PCT No.: PCT/EP2005/003669
§ 371 (c)(1),
(2), (4) Date: Feb. 12, 2008

(87) PCT Pub. No.: WO2005/097068
PCT Pub. Date: Oct. 20, 2005

(65) Prior Publication Data
US 2008/0181854 A1 Jul. 31, 2008

(30) Foreign Application Priority Data

Apr. 8, 2004 (GB) .................................. 0408070.1
Apr. 8, 2004 (GB) .................................. 0408076.8

(51) Int. Cl.
  *A61K 9/12* (2006.01)
  *A61K 47/10* (2006.01)
  *A61K 47/14* (2006.01)
  *A61K 47/38* (2006.01)
  *A61K 9/00* (2006.01)
  *A61K 47/26* (2006.01)

(52) U.S. Cl.
CPC ............... *A61K 9/122* (2013.01); *A61K 9/0014* (2013.01); *A61K 47/10* (2013.01); *A61K 47/14* (2013.01); *A61K 47/26* (2013.01)

(58) Field of Classification Search
None
See application file for complete search history.

(56) References Cited

U.S. PATENT DOCUMENTS

| | | | | |
|---|---|---|---|---|
| 2,198,582 A | * | 4/1940 | Du Vall et al. | 560/67 |
| 3,244,589 A | * | 4/1966 | Sunnen et al. | 424/45 |
| 4,981,678 A | * | 1/1991 | Tomlinson | 424/45 |
| 5,679,324 A | * | 10/1997 | Lisboa et al. | 424/45 |
| 6,440,437 B1 | * | 8/2002 | Krzysik et al. | 424/402 |
| 2001/0031769 A1 | | 10/2001 | Jackman et al. | |
| 2001/0051650 A1 | | 12/2001 | Kriwet et al. | |
| 2005/0031547 A1 | * | 2/2005 | Tamarkin et al. | 424/45 |

FOREIGN PATENT DOCUMENTS

| | | |
|---|---|---|
| WO | 02/080978 | 10/2002 |
| WO | 2004/016289 | 2/2004 |

* cited by examiner

Primary Examiner — Misook Yu
Assistant Examiner — Kauser M Akhoon
(74) Attorney, Agent, or Firm — Crowell & Moring LLP

(57) ABSTRACT

Pharmaceutical foam compositions substantially free of ethanol and comprising pimecrolimus in a carrier vehicle comprising a mixture of oily solvents amounting to at least 40% of the total weight of the composition and consisting of:
i) hexylene glycol;
ii) optionally oleyl alcohol; and
iii) dimethylisosorbide and/or medium chain triglycerides;
and additionally:
iv) when oleyl alcohol is absent, water in an amount of less than 25%;
v) at least one consistency agent;
vi) at least one preservative; and
vii) at least one surfactant/emulgator; and propellant gas for foaming;
and optionally further conventional excipients.
They are indicated for use in the treatment of various skin, nail and mucosal diseases.

4 Claims, No Drawings

PIMECROLIMUS FOAM COMPOSITION CONTAINING HEXYLENE GLYCOL, OPTIONALLY OLEYL ALCOHOL, DIMETHYLISOSORBIDE AND/OR MEDIUM CHAIN TRIGLYCERIDES

The invention relates to pharmaceutical compositions, for use in particular in the treatment of skin diseases. It concerns a pharmaceutical composition comprising the anti-inflammatory ascomycin derivative pimecrolimus in the form of a foam.

WO 2004/016289 discloses topical pharmaceutical compositions substantially free of ethanol and water which comprise an ascomycin in a carrier vehicle comprising a 3-component mixture amounting to at least 40% of the total weight of the compositions and consisting of:
i) a $C_{3-8}$ alkanol and/or $C_{1-8}$ alkanediol;
ii) a fatty alcohol; and
iii) a further solvent selected from:
   a) an alkane carboxylic acid alkyl ester and/or alkane dicarboxylic acid alkyl ester and/or
   b) a hydrophilic co-component and/or
   c) a triglyceride;
and optionally further conventional excipients.

While these compositions are essentially single-phase liquid or semi-solid, it is also envisaged in that disclosure that the liquid phase may form the liquid component of a foam formulation.

It has now been found that, surprisingly, foams comprising the ascomycin pimecrolimus in a particular type of formulation not disclosed as such therein and having a high oil content, while optionally including a small amount of added water, are particularly beneficial.

Specifically, the invention concerns a pharmaceutical foam composition substantially free of ethanol and comprising pimecrolimus in a carrier vehicle comprising a mixture of oily solvents amounting to at least 40% of the total weight of the composition and consisting of:
i) hexylene glycol;
ii) optionally oleyl alcohol; and
iii) dimethylisosorbide and/or medium chain triglycerides;
and additionally:
iv) when oleyl alcohol is absent, water in an amount of less than 25%;
v) at least one consistency agent;
vi) at least one preservative; and
vii) at least one surfactant/emulgator; and propellant gas for foaming;
and optionally further conventional excipients;
hereinafter briefly named "the composition of the invention".

Thus at least 40% of the total weight of the composition is consisting of hexylene glycol, oleyl alcohol, dimethylisosorbide and/or medium chain triglycerides.

In a subgroup the composition of the invention is substantially free of ethanol and water and comprises pimecrolimus in a carrier vehicle comprising a 3-component mixture of oily solvents amounting to at least 40% of the total weight of the composition and consisting of:
i') hexylene glycol;
ii') oleyl alcohol; and
iii') dimethylisosorbide and medium chain triglycerides;
and additionally:
v') at least one consistency agent;
vi') at least one preservative; and
vii') at least one surfactant/emulgator; and propellant gas for foaming;
and optionally further conventional excipients.

In a preferred subgroup thereof the carrier vehicle for pimecrolimus is consisting of:
i') hexylene glycol;
ii') oleyl alcohol; and
iii') dimethylisosorbide and medium chain triglycerides;
and additionally:
v') hydroxypropyl cellulose and/or stearyl alcohol;
vi') p-hydroxybenzoic acid ester with ethyleneglycol phenylether; and
vii') glyceryl monostearate and non-ionic sugar esters; and propellant gas for foaming.

In another subgroup the composition of the invention is substantially free of ethanol and comprises pimecrolimus in a carrier vehicle comprising a 2-component mixture of oily solvents amounting to at least 40% of the total weight of the composition and consisting of:
i") hexylene glycol; and
iii") dimethylisosorbide and/or medium chain triglycerides;
and additionally:
iv") water in an amount of less than 25%;
v") at least one consistency agent;
vi") at least one preservative; and
vii") at least one surfactant/emulgator; and propellant gas for foaming;
and optionally further conventional excipients.

In a preferred subgroup thereof the carrier vehicle for pimecrolimus is consisting of:
i") hexylene glycol; and
iii") medium chain triglycerides and optionally dimethylisosorbide;
and additionally:
iv") water in an amount of less than 25%;
v") polyvinylpyrrolidone and stearyl alcohol;
vi") p-hydroxybenzoic acid ester with ethyleneglycol phenylether; and
vii") glyceryl monostearate and lecithin; and propellant gas for foaming.

The composition of the invention is effective independently of the condition of the skin, nail or mucosa, is well tolerated, stable and has particularly interesting penetration properties.

It retains and improves on the beneficial penetration properties of more complex or inhomogenous formulations such as water- or hydrocarbon-based emulsions or suspensions, while being particularly convenient in terms of ease of administration and patient compliance. It has the advantage of consisting of few components, is straightforward to prepare and well-tolerated on human skin.

Pimecrolimus is the compound of formula I

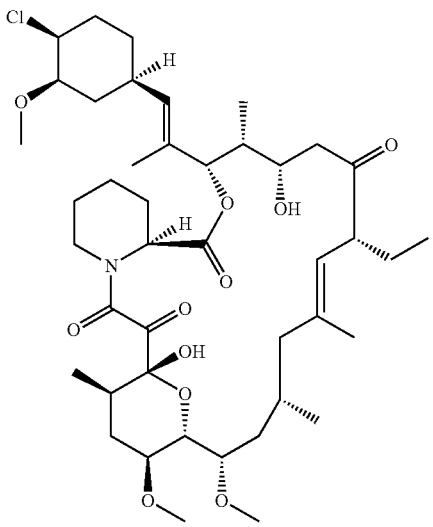 [SMILES: CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@H](Cl)[C@H](OC)C3)[C@H](C)[C@@H](O)CC1=O)[C@H](C)C[C@@H]2OC]

(Example 66a in EP 427680), i.e. {[1E-(1R,3R,4S)]1R,9S, 12S,13R, 14S,17R,18E, 21 S,23S,24R,25S,27R}-12-[2-(4-chloro-3-methoxycyclohexyl)-1-methylvinyl]-17-ethyl-1,14-dihydroxy-23,25-dimethoxy-13,19,21,27-tetramethyl-11,28,dioxa-4-azatricyclo [22.3.1.0(4,9)]octacos-18-ene-2,3,10,16-tetraone.

Hexylene glycol preferably is in an amount of from about 1% to about 10% when component ii) is present, and preferably in an amount of from about 2% to about 20%, preferably from about 5% to about 10% when component iv) is present.

Oleyl alcohol when present preferably is in an amount of from about 1% to about 20%.

Added water when present preferably is in an amount of from about 1% to about 20%, especially from about 5% to about 15%.

Dimethylisosorbide preferably is in an amount of from about 35% to about 90% when component ii) is present, and from about 0% to about 20%, preferably from about 0% to about 10% when component iv) is present.

Medium chain triglycerides preferably are in an amount of from about 5% to about 20% when component ii) is present, and from about 50% to about 80%, preferably from about 60% to about 70% when component iv) is present.

Consistency agents may be conventional, e.g. as disclosed in WO 2004/016289. They preferably are hydroxypropyl cellulose or polyvinylpyrrolidone, and/or stearyl alcohol; when component ii) is present, they preferably are in an amount of from about 0.1% to about 5%, e.g. hydroxypropyl cellulose from about 0.2% to about 1% together with stearyl alcohol from about 1% to about 5%; when component iv) is present, they preferably are in an amount of from about 1% to about 10%, e.g. polyvinylpyrrolidone from about 1% to about 5% together with stearyl alcohol from about 3% to about 10%.

Preservatives may be conventional, e.g as disclosed in WO 2004/016289, preferably they are p-hydroxybenzoic acid esters (parabens), e.g. a p-hydroxybenzoic acid ester with ethyleneglycol phenylether, such as Phenonip®. They preferably are in an amount of from about 0.1% to about 0.5%.

Surfactants/emulgators for foaming may be conventional, e.g. cationic, non-ionic or anionic, e.g. cetrimide, lecithin, soaps and silicones. Commercially available surfactants such as Tween® are also suitable. Preferred are glyceryl monostearate, lecithin and non-ionic sugar. esters, such as Sistema SP-30 and SP-70. When component ii) is present, the amount of surfactant/emulgator is from about 0.5% to about 5%, e.g. glyceryl monostearate from about 1% to about 3%, together with Sistema SP-30 and SP-70, each from about 0.5% to about 2%. When component iv) is present, the amount of surfactant/emulgator is from about 0.5% to about 20%, e.g. glyceryl monostearate from about 1% to about 3%, together with lecithin from about 5% to about 20%.

The propellant gas for foaming is e.g. any harmless gas conventionally used as a propellant, such as butane or propane, or a mixture of butane and propane, e.g. in the ratio about 80/20.

"Substantially free of ethanol" and "substantially free of water" means that neither ethanol nor, respectively, water is added as an intentional constituent part of the composition of the invention. However, e.g. a small amount of humidity, e.g. up to about 1% water, may nevertheless be present, e.g. as an intrinsic impurity in some of the excipients used, or as part of the active ingredient when this is e.g. a hydrate, e.g. when crystal form A (see WO 99/01458) of pimecrolimus is used.

"%" herein means percent on a weight by weight (w/w) basis.

"Total weight of the composition" is to be understood as referring to the total weight including surfactant/emulgator, but without propellant gas.

A particularly beneficial aspect of the composition of the invention is that while the components of the above oily solvents are solubilizing agents, they additionally may possess penetration enhancing properties, thus contributing to keeping the formulation both simple and effective.

"Treatment" as used herein includes prevention, namely prophylactic as well as curative treatment.

The active agent component may be in free form or pharmaceutically acceptable salt form if such forms exist.

The invention thus provides a formulation for application to a body surface as a foam, comprising the active ingredient pimecrolimus and a foamable carrier vehicle as defined above. The active ingredient may be present as an integral part of the formulation, or some components may be held separately to other ingredients of the formulation and be combined therewith during formation of the foam. The formulation comprises a foaming agent (particularly, at least one surfactant/emulgator) which is capable of promoting production of a foam structure.

The invention therefore also provides a foamable carrier and an active ingredient with some components of the carrier packaged separately thereto, which are admixed with the other components during the foaming process.

The foam may be exposed to the atmosphere so that it dries into a coating, or may be covered by conventional dressings.

The composition of the invention is applied to the body site of interest in the form of a foam and it is therefore necessary that the composition undergoes a foaming process before application to the body. In the foaming process gas is forced into or is formed within the formulation to entrap small bubbles of gas therein, thereby forming the foam. Any suitable gas or gas producing system can be used to produce the foam, e.g. butane, propane and nitrous oxide, but other gases are also suitable. Normally the foam is produced by conventional means such as aerosol technology.

The composition may be stored in any convenient container until required. Generally, the container is designed to preserve the sterile nature of the formulation. The container will conveniently be provided with means to foam the composition when required.

The invention thus also provides a closed container containing a composition of the invention, capable of expelling the formulation in the form of a foam. For example, the container may be an aerosol canister, containing a pressurized gas which in use causes production of the foam. Alternatively, the gas may be produced by a chemical reaction when two different ingredients, contained in e.g. two portions of a sachet, are mixed together. The closed container may have separate reservoirs for the foamable carrier or parts thereof and the active ingredient. Thus the foamable carrier or parts thereof and the active ingredient are stored separately during storage and are admixed together in suitable proportions during the foaming process.

The invention also provides an apparatus to produce a foam for application to a body surface from a composition of the invention, comprising:
a) a closed container having a reservoir containing the foamable carrier or parts thereof, and a reservoir containing the active ingredient and the remaining parts of the carrier; and
b) means to produce a foam from the foamable carrier.

Optionally further foaming agents may be mixed with the foamable carrier.

The gel may be sterilised and this is generally desirable for medical use. Sterilisation may take place by autoclaving the composition, e.g. at temperatures of from about 100° C. to about 125° C., e.g. for less than 30 minutes.

The advantages of applying a topical product in the form of a foam include:
easy and rapid application;
conformity to surface irregularities;
insulation of the diseased area;
cooling of the tissues;
antibacterial action to prevent infection;
biocompatibility with tissue; and/or
maintenance of a moist environment.

The foam produced may subside over a period of time, e.g. 3 to 24 hours, as some of the gas entrapped in the foam structure escapes. The foamed composition gradually dries to produce a foam sheet which still retains a basic foam structure and which may cover the site to which the foam was applied. This foam sheet can be left in place as a protective cover.

The composition of the invention will normally be applied directly to the body site of interest in the form of a foam produced from a suitable device, such as an aerosol, immediately before administration. It is, however, possible to preproduce an amount of the foamed composition which is then applied onto the body site by any suitable means, e.g. by hand or by spatula.

The composition of the invention may optionally comprise further conventional excipients, such as plasticizers, humectants (e.g. glycerol, propane-1,2-diol, polypropylene glycol and other polyhydric alcohols), free radical scavengers, anti-oxidants, viscosity-adjusting agents, dyes and colorants, e.g. as described in H. P. Fiedler, "*Lexikon der Hilfsstoffe für Pharmazie, Kosmetik und angrenzende Gebiete*", Editio Cantor Verlag Aulendorf, Aulendorf, 5th Edition (2002).

The composition of the invention is indicated for use in the treatment of inflammatory and hyperproliferative skin diseases and of cutaneous manifestations of immunologically-mediated diseases. The terms "skin" and "cutaneous" should be understood broadly as comprising also diseases of e.g. nail or mucosa. Examples of immunologically-mediated diseases include alopecia areata, psoriasis, atopic dermatitis, contact dermatitis and further eczematous dermatitises, seborrhoeic dermatitis, lichen planus, pemphigus, bullous pemphigoid, epidermolysis bullosa, urticaria, angioedemas, vasculitides, erythemas, cutaneous eosinophilias, and lupus erythematous. Examples of skin diseases include dermatomyositis, leukoderma vulgaris, ichthyosis vulgaris, photoallergic sensitivity, cutaneous T cell lymphoma, acne, autoimmune diseases such as chronic rheumatoid arthritis, scleroderma and the like.

The invention further provides a composition as defined above for use in the treatment of inflammatory and hyperproliferative skin diseases and of cutaneous manifestations of immunologically-mediated diseases.

It further provides a method for treating inflammatory and hyperproliferative skin diseases or cutaneous manifestations of immunologically-mediated diseases comprising administering a composition of the invention to a patient in need thereof.

Still further, it provides the use of a composition of the invention in the preparation of a medicament for the treatment of inflammatory and hyperproliferative skin diseases and of cutaneous manifestations of immunologically-mediated diseases.

It further provides the use of a carrier vehicle as defined above to enhance penetration of pimecrolimus into human skin, nail or mucosa.

The composition of the invention may be prepared in conventional manner by working up the components into a pharmaceutical composition. For example, the composition of the invention may be obtained by dissolving pimecrolimus in hexylene glycol and/or oleyl alcohol or medium chain triglycerides, and other components, e.g. dimethylisosorbide and the further excipients, may be added at the appropriate time as is conventional.

The following Examples illustrate the invention. The compounds are in free, i.e. neutral or base form unless specified otherwise.

EXAMPLE 1

Foam

| Component | Amount (g) |
|---|---|
| Pimecrolimus | 1.0 |
| 1) Oily solvents: | |
| i) hexylene glycol | 2.5 |
| ii) oleyl alcohol | 2.5 |
| iii) dimethylisosorbide (Arlasolve$^R$) | 77.2 |
| medium chain triglycerides (oil) | 10.0 |
| 2) Consistency agents: | |
| hydroxypropyl cellulose (Klucel MF) | 0.5 |
| stearyl alcohol | 2.0 |
| 3) Preservative: | |
| Phenonip$^R$ (a p-hydroxybenzoic acid ester with ethyleneglycol phenylether) | 0.3 |
| 4) Surfactants/emulgators: | |
| glyceryl monostearate | 2.0 |
| Sisterna SP-30 and SP-70 (=non-ionic sugar esters, mild emulgators) | 1.0 (each) |
| Total | 100.0 |
| 5) Propellant: | |
| butane/propane 80/20 | |

The preparation is according to conventional manufacturing procedures for a foam.

EXAMPLE 2

Foam

| Component | Amount (g) |
|---|---|
| Pimecrolimus | 1.0 |
| 1) Oily solvents: | |
| i) hexylene glycol | 10.0 |
| ii) medium chain triglycerides (oil) | 59.7 |
| 2) Water | 10.0 |
| 3) Consistency agents: | |
| polyvinylpyrrolidone (PVP K90) | 2.0 |
| stearyl alcohol | 5.0 |
| 4) Preservative: | |
| Phenonip$^R$ (a p-hydroxybenzoic acid ester with ethyleneglycol phenylether) | 0.3 |
| 5) Surfactants/emulgators: | |
| glyceryl monostearate | 2.0 |
| lecithin | 10.0 |
| Total | 100.0 |
| 6) Propellant: | |
| butane/propane 80/20 | |

The preparation is according to conventional manufacturing procedures for a foam.

EXAMPLE 3

Foam

As for Example 2, whereby as solvent i) only 5.0 g hexylene glycol is used, and as solvent ii) 5.0 g dimethylisosorbide is included in addition to the triglycerides.

The invention claimed is:

1. A pharmaceutical foam composition substantially free of ethanol and consisting of pimecrolimus in a carrier vehicle consisting of:
   i) hexylene glycol;
   ii) dimethylisosorbide and/or medium chain triglycerides;
   iii) water in an amount of 5% to 15%;
   iv) at least one consistency agent selected from the group consisting of hydroxypropyl cellulose, polyvinylpyrrolidone and stearyl alcohol;
   v) p-hydroxybenzoic acid ester with ethyleneglycol phenylether as a preservative;
   vi) at least one surfactant/emulgator for foaming selected from the group consisting of glycerol monostearate, non-ionic sugar esters, and lecithin; and
   vii) butane/propane 80/20 as a propellant gas for foaming.

2. A composition according to claim 1 consisting of pimecrolimus in a carrier vehicle consisting of:
   i') hexylene glycol;
   ii') dimethylisosorbide and medium chain triglycerides;
   iii') water in an amount of 10%;
   iv') hydroxypropyl cellulose and stearyl alcohol;
   v') p-hydroxybenzoic acid ester with ethyleneglycol phenylether;
   vi') glyceryl monostearate and non-ionic sugar esters; and
   vii') butane/propane 80/20 as a propellant gas for foaming.

3. A composition according to claim 1 consisting of pimecrolimus in a carrier vehicle consisting of:
   i") hexylene glycol;
   ii") medium chain triglycerides;
   iii") water in an amount of 10%;
   iv") polyvinylpyrrolidone and stearyl alcohol;
   v") p-hydroxybenzoic acid ester with ethyleneglycol phenylether;
   vi") glyceryl monostearate and lecithin; and
   vii") butane/propane 80/20 as propellant gas for foaming.

4. A method for treating inflammatory and hyperproliferative skin diseases or cutaneous manifestations of immunologically-mediated diseases comprising administering a composition according to claim 1 to a patient in need thereof.

* * * * *